(12) United States Patent
Doi et al.

(10) Patent No.: US 6,864,780 B2
(45) Date of Patent: Mar. 8, 2005

(54) DATA TRANSMISSION SYSTEM USING A HUMAN BODY AS A SIGNAL TRANSMISSION PATH

(75) Inventors: Kenji Doi, Nara (JP); Masaru Hashimoto, Osaka (JP); Masaki Koyama, Osaka (JP); Yoshiko Suzuki, Moriguchi (JP); Tokuhisa Nishimura, Shijonawate (JP)

(73) Assignee: Matsushita Electric Works, Ltd., Kadoma (JP)

( * ) Notice: Subject to any disclaimer, the term of this patent is extended or adjusted under 35 U.S.C. 154(b) by 390 days.

(21) Appl. No.: 09/948,638

(22) Filed: Sep. 10, 2001

(65) Prior Publication Data

US 2002/0030585 A1 Mar. 14, 2002

(30) Foreign Application Priority Data

Sep. 8, 2000 (JP) .......................... 2000-272984

(51) Int. Cl.$^7$ .......................... G08B 29/00; H04B 1/00; G08C 19/00
(52) U.S. Cl. ................................ 340/5.64; 340/825.72
(58) Field of Search ...................... 340/565, 5; 341/176

(56) References Cited

U.S. PATENT DOCUMENTS

| | | | |
|---|---|---|---|
| 4,591,854 A | | 5/1986 | Robinson |
| 5,062,232 A | * | 11/1991 | Eppler ........................ 42/70.11 |
| 5,796,827 A | | 8/1998 | Coppersmith et al. |
| 5,811,897 A | | 9/1998 | Spaude et al. |
| 6,223,018 B1 | * | 4/2001 | Fukumoto et al. .......... 455/41.1 |
| 6,324,053 B1 | * | 11/2001 | Kamijo ........................ 361/683 |
| 6,350,129 B1 | * | 2/2002 | Gorlick ........................ 439/37 |

FOREIGN PATENT DOCUMENTS

| | | |
|---|---|---|
| EP | 0 843 425 | 5/1998 |
| JP | 61-46639 | 3/1986 |
| JP | 10-229357 | 8/1998 |
| JP | 2001-77735 | 3/2001 |
| WO | WO 87/03119 | 5/1987 |
| WO | WO 96/36134 | 11/1996 |

* cited by examiner

Primary Examiner—Michael Horabik
Assistant Examiner—Scott Au
(74) Attorney, Agent, or Firm—Oblon, Spivak, McClelland, Maier & Neustadt, P.C.

(57) ABSTRACT

A data transmission system using a human body as a signal transmission path includes a transmitter and a receiver. The transmitter uses a pair of electrodes which are held in close proximity to the skin of the human body. The transmitter transmits data to the receiver through the signal transmission path partly extending through the human body when a user carrying the transmitter touches a touch electrode of the receiver. The electrodes are integrated into a garment worn by the user in such a manner that the electrodes are kept in a closely facing relation to the skin of the user, thereby establishing the electrical path extending through the human body. With the integration of the two electrodes into the garment, the user wearing the garment as an everyday clothes or uniform can be easy and convenient to carry the transmitter for successful transmission of the data.

7 Claims, 6 Drawing Sheets

DATA TRANSMISSION SYSTEM USING A HUMAN BODY AS A SIGNAL TRANSMISSION PATH

BACKGROUND ART

1. Field of the Invention

The present invention relates to a data transmission system using a human body as a signal path, and more particularly to a system composed of a wearable transmitter, a receiver adapted to be connected to an associated equipment which utilize data transmitted from the transmitter, and a garment integrally holding two electrodes for passing the data through the human body.

2. Description of the Prior Art

U.S. patent application Ser. No. 09/605,357 discloses a data transmission system using the human body as a signal path. The system includes a portable transmitter in the form of a wrist watch to be worn on a user, and a signal receiver. The transmitter has a pair of electrodes on the back of the wrist watch for direct contact with the skin of the user. One electrode acts as a signal electrode which is connected through a portion of the user's body to a touch electrode of the signal receiver, while the other electrode acts as a ground electrode which is coupled through the other portion of the user's body to a circuit ground of the signal receiver to complete a signal path through the user's body for data transmission from the wrist watch to the signal receiver. When using this system used for a verified access to a place or database, however, the user is always required to keep in mind to carry the dedicated wrist watch having the electrodes. This may be sometimes inconvenient and even troublesome for the user who has his own wrist watch.

SUMMARY OF THE INVENTION

In view of the above inconvenience, the present invention has been achieved to provide a data transmission system which is capable of assuring successful data transmission without requiring a special attention to the user. The system in accordance with the present invention comprises a transmitter adapted to be carried by the user and a receiver adapted to be connected to an associated equipment which utilizes data transmitted from the transmitter. The transmitter has a ground electrode to be placed in close proximity to the human body, a signal electrode to be placed also in close proximity to the human body in a spatially spaced relation from the ground electrode, a data memory storing first data, a first modulator for converting the first data into a first modulated voltage signal, and a first signal transmitter which applies the first modulated voltage signal across the signal electrode and the ground electrode. The receiver includes a circuit ground adapted to be connected to the ground, a touch electrode adapted for direct contact with a portion of the human body carrying the transmitter, a signal detector connected across the signal electrode and the circuit ground to detect the first modulated voltage signal, and a demodulator which converts the first modulated voltage signal back into the first data. The characterizing feature of the present invention resides in that the system includes a garment which is adapted to be worn by a user and integrates the ground and signal electrodes in such a manner that at least one of the electrodes is kept in a closely facing relation to the skin of the user, thereby establishing an electrical path extending through a portion of the human body for signal transmission from the transmitter to the receiver. With the integration of the two electrodes into the garment, the user wearing the garment as an everyday clothes or uniform such as a white gown can be easy and convenient to carry the transmitter for successful transmission of the data to the receiver.

Preferably, each of the ground and signal electrodes is formed by a plurality of electrically conductive threads and is sewed to be integrated into the garment. Thus, the electrodes can be easily integrated into the garment and cannot sacrifice comfortableness of the garment. Each electrode made of the electrically conductive threads can be woven into a fabric so as to be lined on the garment. Alternatively, the electrode of the conductive threads can be woven into an indispensable part of the garment. With the use of the electrical conductive threads, the garment provided with the resulting electrodes can be washed like ordinary clothes, which enhances availability of the system.

The ground electrode is preferred to be located on the garment closer to the foot of the user than the signal electrode for establishing a consistent electrical path through the human body. That is, the electrical path is composed of a first fraction path extending from the ground electrode down to the foot of the user and through the ground to the circuit ground of the receiver, and a second fraction path extending from the signal electrode towards and through a finger of the user to the touch electrode of the receiver without interfering the first fraction path, thereby assuring efficient and reliable data transmission.

In a preferred embodiment where both of the ground and signal electrodes are held on the garment so as to come into a closely facing relation with the skin of the user, the transmitter has a case which accommodates an electrical circuitry realizing the first modulator and the first signal transmitter, and which is formed as a separate article from the electrodes. The case is provided with terminals for electrically connecting the circuitry with the ground and signal electrodes. In this connection, the garment is additionally provided with a ground lead and a signal lead which extend respectively from the ground and signal electrodes for connection with the terminals of the case. Both of the ground and signal leads are formed by a strand of the electrically conductive threads and are sewed on the garment. Thus, the leads can be also easily and consistently integrated into the garment to retain comfortableness of the garment.

A coupling member is included in the system to make the case detachable from the garment and at the same time make the electrical circuitry detachable from the electrodes, i.e., the corresponding leads. The coupling member may be realized by a spring-loaded clip which is pivotally supported to the case so as to be movable between a pinching position and a release position. The clip is formed with the terminals which are electrically isolated from each other for connection respectively with the ground and signal leads at the pinching position.

Instead of the clip, the coupling member may comprise a pair of first fasteners each composed of one of a socket and a ball forming a snap button for mounting the case to the garment, and a pair of second fasteners each composed of the other of the socket and the ball. The first fasteners are fixed on the case and connected across the first signal transmitter of the circuitry, while the second fasteners are fixed on the garment and are permanently connected to respectively to the ground and signal electrodes. When using the snap button to make the case detachable from the garment, the second fasteners are preferably held in direct contact with the ground and signal electrodes, respectively formed of the electrically conductive threads, thereby substantially eliminating the leads from the garment. In this connection, the ground and signal electrodes may be in the form of annular bands provided inside of a sleeve of the garment in a spaced relation from each other along the length of the sleeve.

Preferably, the case is made water-tight for sealing the electric circuitry so that the garment can be washed like ordinal clothes even with the case. Further, the case may be in the form of a plate which encapsulate the circuitry and a battery energizing the circuitry. Thus, the plate can be utilized also as a nameplate as is usual with the white gown worn by a physician, nurse, and a laboratory worker.

These and still other objects and advantageous features will become more apparent from the following description of the preferred embodiments when taken in conjunction with the attached drawings.

DETAILED DESCRIPTION OF THE EMBODIMENTS

Figure 1:
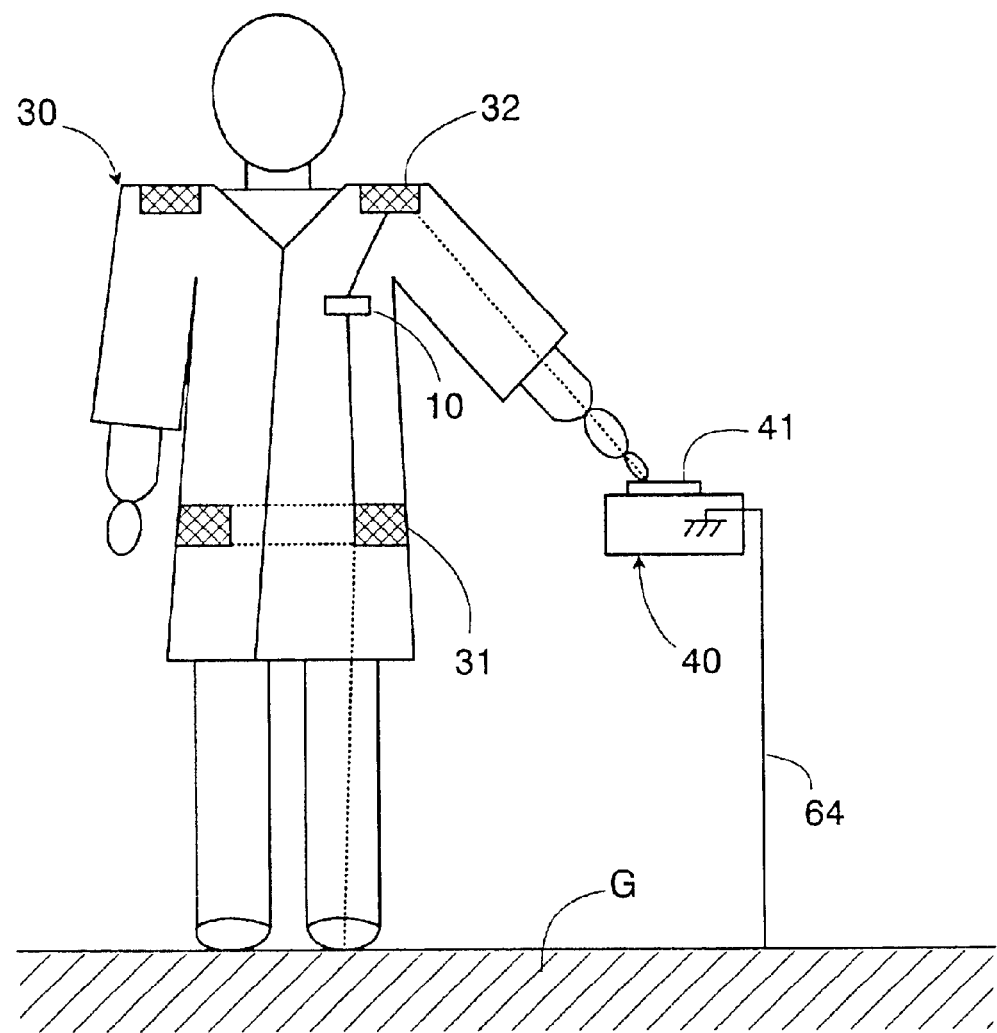
FIG. 1 is a schematic view illustrating a basic concept of a data transmission system in accordance with the present invention.

Referring first to FIG. 1, there is shown a principle of a data transmission system using a human body as a signal transmission path. The system includes a wearable transmitter 10 adapted to be worn on the human body, and a receiver 40 adapted to be connected to an equipment such as a personal computer 60 which utilizes data transmitted from the transmitter for controlled operation of the computer 60, for example, a verified log-in of the user. The transmitter 10 is connected to a ground electrode 31 and a signal electrode 32 which are integrated into a garment 30 worn by a user in close proximity to the skin of the user. When the user carrying the transmitter 10 touches a touch electrode 41 of the receiver 40, a signal path is established which extends from the signal electrode 32 through a portion of the user's body, the touch electrode 41, an internal circuit of the receiver 40, a circuit ground 49 of the receiver 40, the ground G, the other portion of the user's body, the ground electrode 31 and an internal circuit of the transmitter 10. The signal path extending through the human body is indicated by dotted lines. Thus, a voltage signal applied across the electrodes 31 and 32 is transmitted to the receiver 40 when the user touches the touch electrode 41. In FIG. 1, the circuit ground of the receiver 40 is connected to the ground G through a ground line 64 common to the computer 60 for the sake of simplicity. However, the circuit ground may be capacitively connected to the ground G or even capacitively connected directly to the major portion of the user's body for establishing the signal path.

Figure 2:
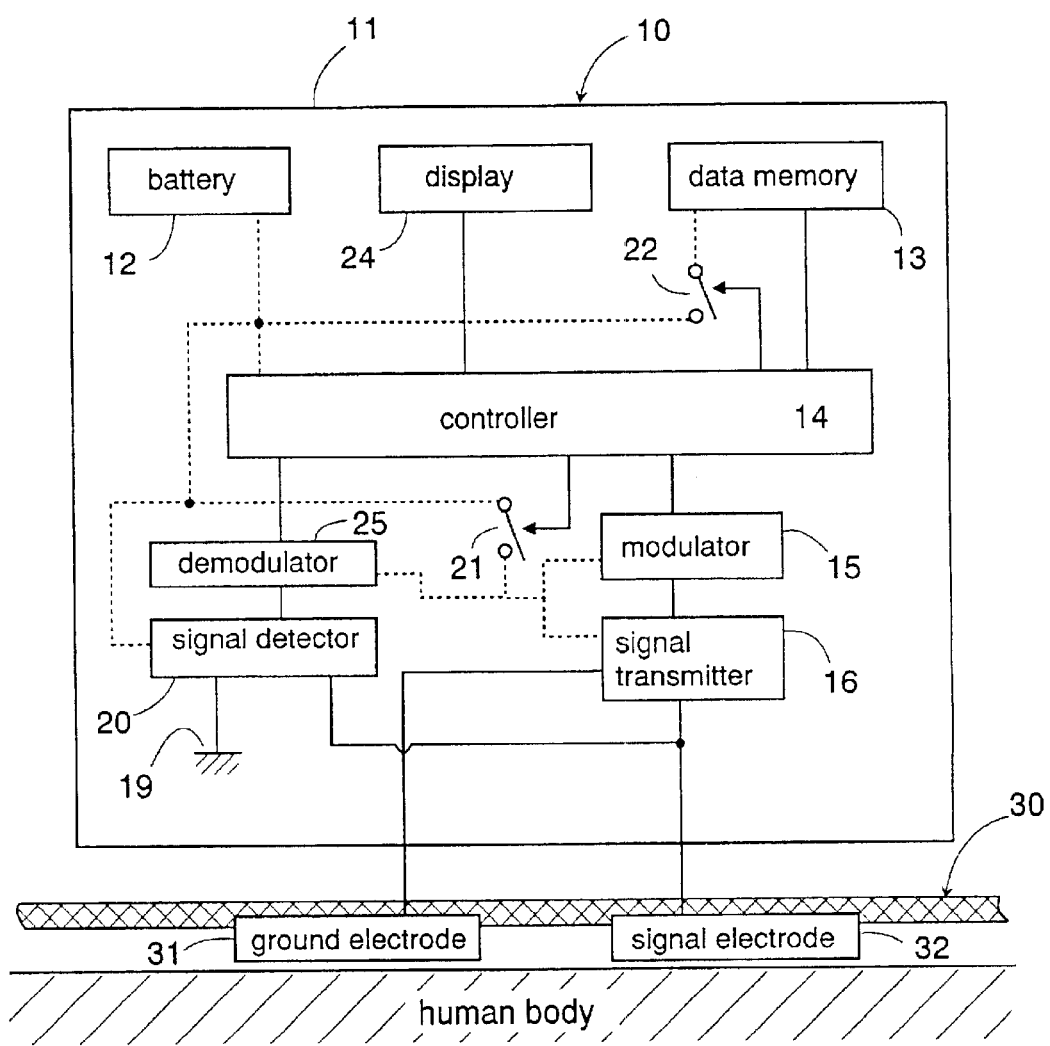
FIG. 2 is a block diagram of a wearable transmitter utilized in the above system.

As shown in FIG. 2, the transmitter 10 includes an electric circuitry and a battery 12 which are accommodated within a case 11. The circuitry includes a data memory 13 storing data to be transmitted, a controller 14, a modulator 15 modulating the data into a modulated voltage signal, a signal transmitter 16 applying the modulated voltage signal across the signal electrode 32 and the ground electrode 31 on the garment 30. Also included in the circuitry is a signal detector 20 which is connected to detect a start signal transmitted from the receiver 40 through the signal electrode 32. The start signal is received across the signal electrode 32 and a circuit ground 19. The circuit ground 19 may be connected to the ground electrode 31. Only the controller 14 and the signal detector 20 are constantly energized by the battery 12 to be ready for detecting the start signal from the receiver 40. In the non-operative condition where the transmitter 10 is not transmitting the data, the controller 14 is kept in a sleep mode of consuming less electric current from the battery 12. When the start signal is received as a consequence of the user touching the touch electrode 41, the signal detector 20 wakes up the controller 14 which in turn energizes the data memory 13, the modulator 15, and the signal transmitter 16 to apply the modulated voltage signal across the signal electrode 32 and the ground electrode 31 for initiating the data transmission. The controller 14 incorporates a timer which starts upon detection of the start signal to provide a predetermined time during which the data is transmitted. After the elapse of the predetermined time, the controller 14 responds to deenergize the modulator 15, the signal transmitter 16 and the data memory 13. For this purpose, the controller 14 includes power switches 21 and 22 which are actuated by the signal detector 20 and the timer to selectively energize and deenergize the modulator 15, the signal transmitter 16 and the data memory 13. Dotted lines in FIG. 2 show power supply lines from the battery 12. Thus, after transmitting the data, the controller 14 goes back into the sleep mode of consuming less current or energy but being kept ready to detect of the start signal for another data transmission. The transmitter 10 optionally includes a display 24 for visual indication of the data stored in the data memory 15.

Figure 3:
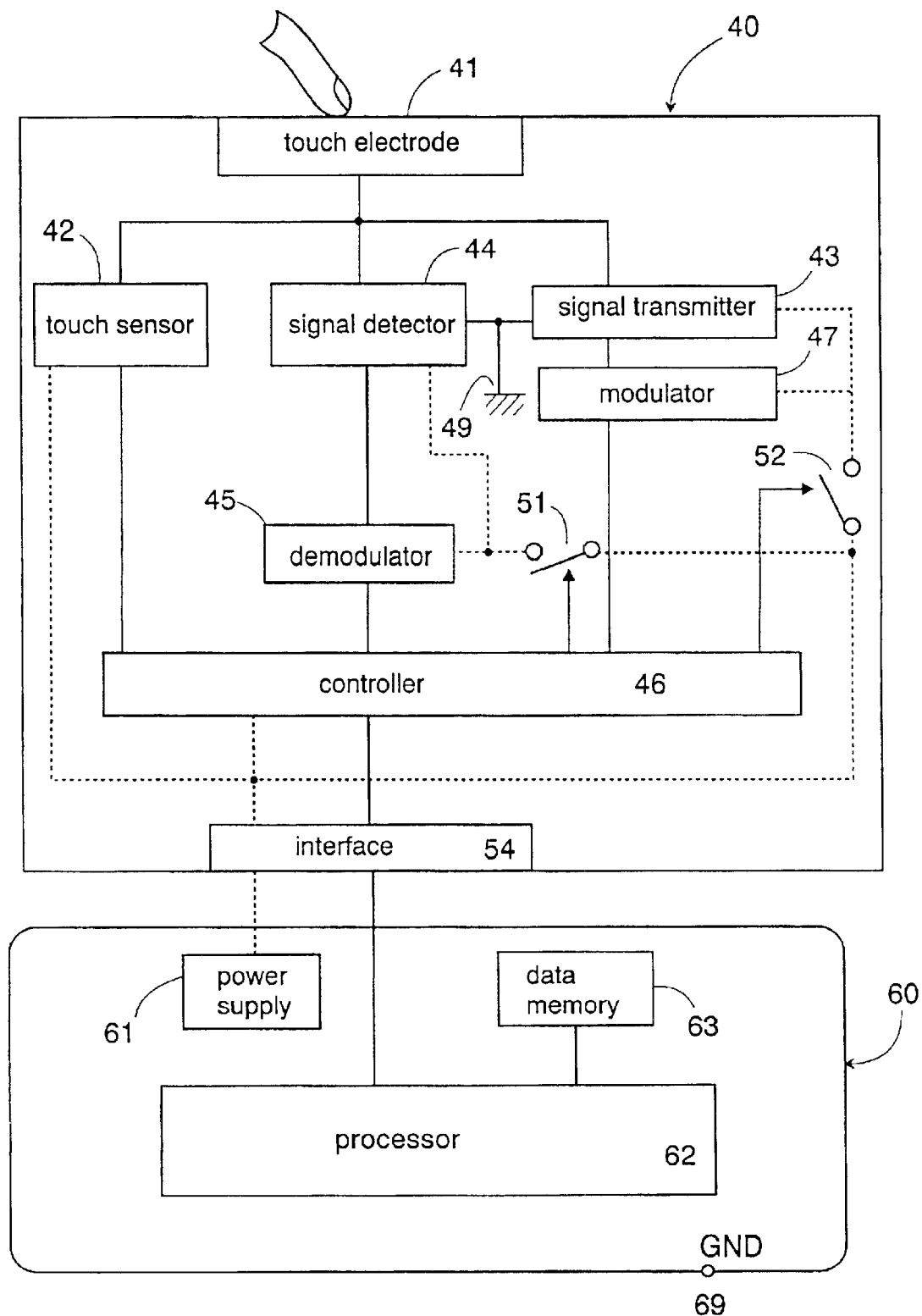
FIG. 3 is a block diagram of an associated receiver utilized in the above system.

As shown in FIG. 3, the receiver 40 includes various circuits connected to the touch electrode 41 on the exterior of a housing of the receiver. The circuits are energized by a power source 61 provided in the computer 60 to which the receiver 40 is attached. The circuits are commonly connected to a circuit ground 49 which is in turn connected to a ground terminal 69 of the computer for connection with the ground. The circuits include a touch sensor 42 which is connected to the touch electrode 41 to give a touch signal when the touch electrode 41 is touched by the user's body. Also included in the circuits are a start signal generator 43, a signal detector 44, a demodulator 45, and a controller 46 which controls the operations of the circuits. The signal transmitter 43 applies the start signal to the touch electrode 41 in response to the touch signal. The signal detector 44 detects the modulated voltage signal which is transmitted from the transmitter 10 and received across the touch electrode 41 and the circuit ground 49. The modulated voltage signal thus detected is demodulated at the demodulator 45 to derive the first data which is then fed to the computer 60 to be processed thereat. For example, the first data includes a user's identification code which is verified at a processor 62 of the computer with reference to various codes assigned to different users and stored in a data memory 63. When the user's ID is verified as a correct one, the computer completes the log-in sequence to permit the access by the user.

Under the non-operating condition where the touch electrode 41 is not touched by the human body, only the controller 46 and the touch sensor 42 are energized to be ready for detection of the touching. Upon the touch electrode 41 being touched, the touch sensor 42 gives the touch signal to the controller 46 which responds to close switches 51 and 52 to energize the signal transmitter 43, the signal detector 44, and the demodulator 45, thereby generating the start signal and making the circuits ready for receiving the data from the transmitter 10. The controller 46 also includes a timer which starts, upon receiving the touch signal, to provide a predetermined time interval during which the data transmission from the first transceiver 10 is expected to complete. After the elapse of the predetermined time interval, the controller 46 responds to open the switches 51 and 52, deenergizing the signal transmitter 43, the signal detector 44, and the demodulator 45. Thus, the receiver 40 is kept in a sleep mode of consuming less electricity until the touch electrode 41 is touched. Dotted lines in FIG. 3 show power supply lines. The receiver 40 further includes an interface 54 in the form of the USB for transferring the data to the computer 60 as well as for receiving the power from a power supply 61.

Further, the transmitter 10 and the receiver 40 are designed to effect a bilateral data transmission therebetween. For this purpose, the transmitter 10 additionally includes a demodulator 25 for demodulating data transmitted from the receiver 40 and that the receiver 40 additionally includes a modulator 47 for modulating the data to be transmitted from the receiver 40. The modulator 47 of gives a modulated voltage signal indicative of the data to be transmitted to the transmitter 10. The signal transmitter 43 of the receiver 40 is responsible for applying the modulated voltage signal to the touch electrode 41 for data transmission back to the transmitter 10.

In operation, when the user touches the touch electrode 41 of the receiver 40, the touch sensor 42 provides a touch signal in response to which the controller 46 energizes the modulator 47, the signal transmitter 43, the demodulator 45, and the signal detector 44. At first, the controller 46 retrieves the data from the data memory 63 of the computer 60 and instructs to give and apply the modulated voltage signal indicative of the data. In response to the voltage signal from the receiver 40, the controller 14 of the transmitter 10 activates the data memory 13 and performs a suitable processing of the data from the data memory 13 in consideration of the data received from the receiver 40. The controller 14 updates the data of the data memory 13 depending upon the result of the processing. Thereafter, the controller 14 activates the modulator 15 and the signal transmitter 16 so as to transmit the modulated voltage signal indicative of the updated data to the receiver 40 through the electrodes 31 and 32. The modulated voltage signal received at the receiver 40 is converted into the data which is utilized by the controller 46 for a controlled operation of the computer or passed to another equipment to be processed thereat for a specific operation of the equipment. In this manner, the two-way data transmission is made between the transmitter and the receiver in a half-duplex manner. Depending upon a specific application to which the system is applied, the system may be designed to have more than one data transmission cycles in which the one-way data transmission from either of the transmitter and the receiver repeats twice or more. In such case, the data in the data memory 13 of the transmitter 10 is modified or updated by the data transmitted from the receiver 40.

Also, for minimizing energy consumption, the transmitter 10 is kept in the sleep mode until the modulated voltage signal is received from the receiver 40, and comes back again in the sleep mode after the data transmission between the transmitter and the receiver is completed. In other words, the data memory 13, the modulator 15, the signal transmitter 16, and the demodulator 21 are energized by closure of the switches 21 and 22 only for a predetermined time period starting from receiving the modulated voltage signal from the receiver. It is within the predetermined time period that the data transmission between the transmitter and the receiver is completed. Likewise, the receiver is kept in the sleep mode until the touch electrode 41 is touched by the human body, and come back to the sleep mode after the data transmission between the first and second transceivers are completed. Thus, the signal transmitter 43, the modulator 47, the signal detector 44, and the demodulator 45 are energized by closure of switches 51 and 52 only for a predetermined time period starting from the touch electrode being touched.

Figure 4:
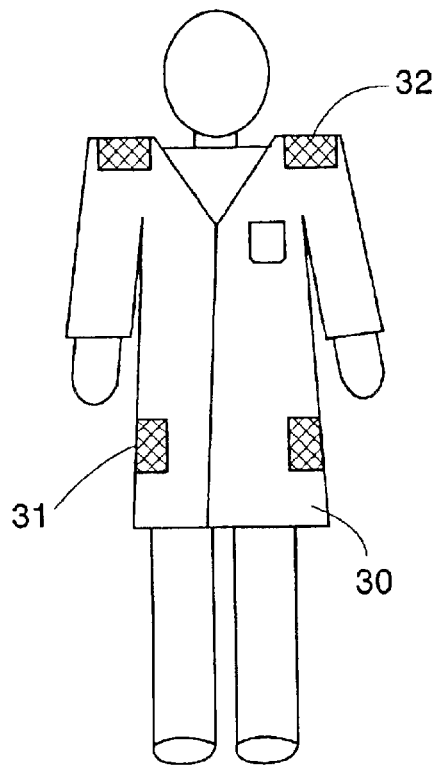
FIGS. 4 and 5 are front and rear views of a garment utilized in the above system to integrate a ground electrode and a signal electrode.
Figure 5:
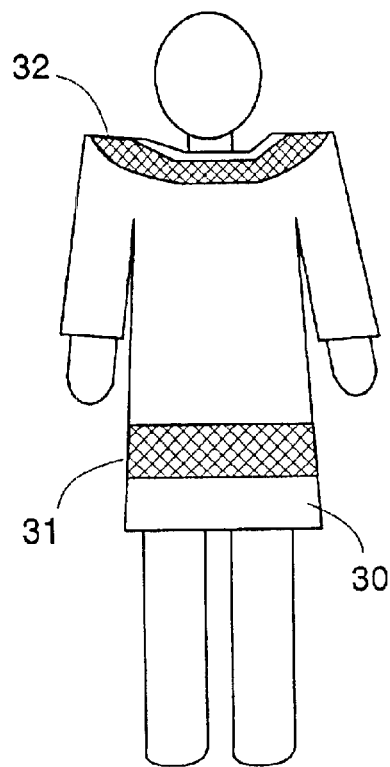
Figure 6:
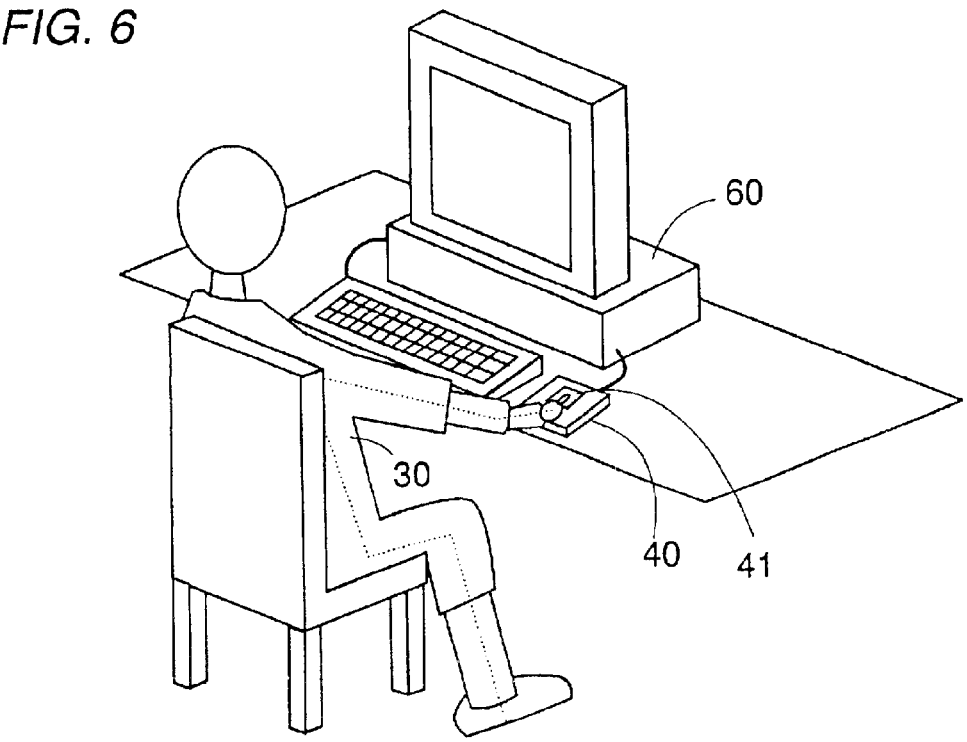
FIG. 6 is a perspective view showing one typical application of the above system.

As shown in FIGS. 1, 4, and 5, the garment 30 to which the electrodes 31 and 32 are attached is selected, for example, as a white gown that is always worn by a particular user like a physician, nurse, and laboratory worker while engaging a job requiring a verification of the user. As a matter of course, the garment 30 is not limited to the white gown and may take various types of the clothes such as a uniform for an office, factory, school, and the like organization or group. Each of the ground electrode 31 and the signal electrode 32 is in the form of a fabric made by electrically conductive threads and is sewed on the inner surface of the garment 30 with the signal electrode 32 disposed at the shoulders of the garment 30 and with the ground electrode 31 disposed around the lower part of the garment corresponding to a hip and buttocks of the user, as shown in FIGS. 4 and 5. Instead of being lined on the garment, the electrodes may be woven into the garment as indispensable parts thereof. The above selected location of the electrodes 31 and 32 is particularly effective when the user access the computer 60 while sitting on a chair as shown in FIG. 6. In this condition, the ground electrode 31 receives a counter force from the seat of the chair to be pressed against the buttocks of the user, while the signal electrode 32 is pressed against the shoulders of the user with the help of weight of the garment for reliable electrical connection of the electrodes to the human body. It is noted in this connection that the ground electrode 31 is located closer to the foot of the user than the signal electrode 32 along the signal path extending through the human body so that the path extending from the signal electrode 32 toward the finger of the user can be substantially free from, i.e., cannot be substantially interfered with the path extending from the ground electrode 31 to the foot of the user for reliable signal transmission between the transmitter 10 and the receiver 40.

Figure 7:
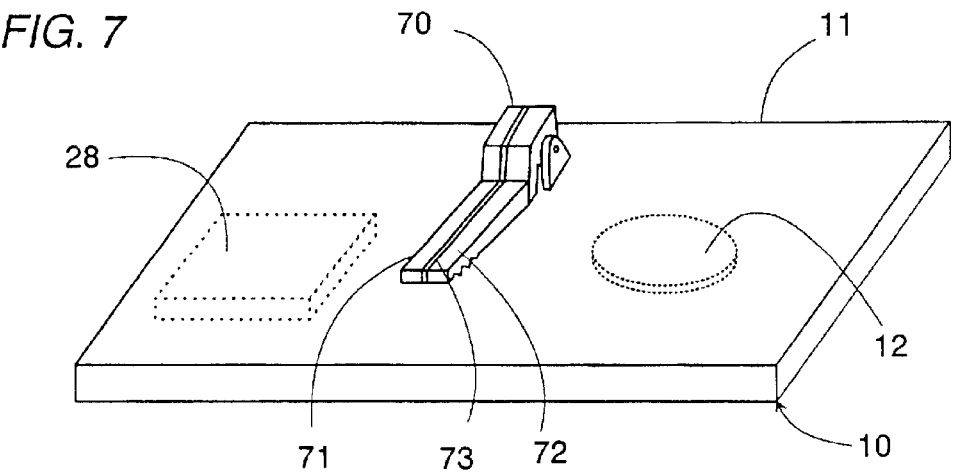
FIG. 7 is a rear perspective view of a case in the form of a nameplate accommodating an electric circuitry of the transmitter and detachable to the garment.
Figure 8:
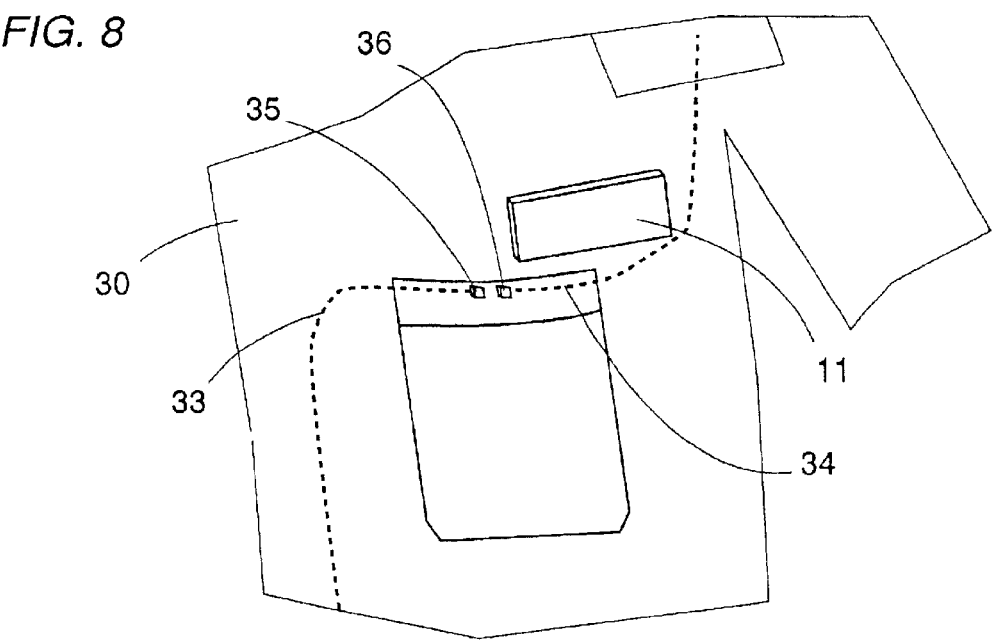
FIG. 8 is a perspective view of the case and a portion of the garment to which the case is attached.
Figure 9:
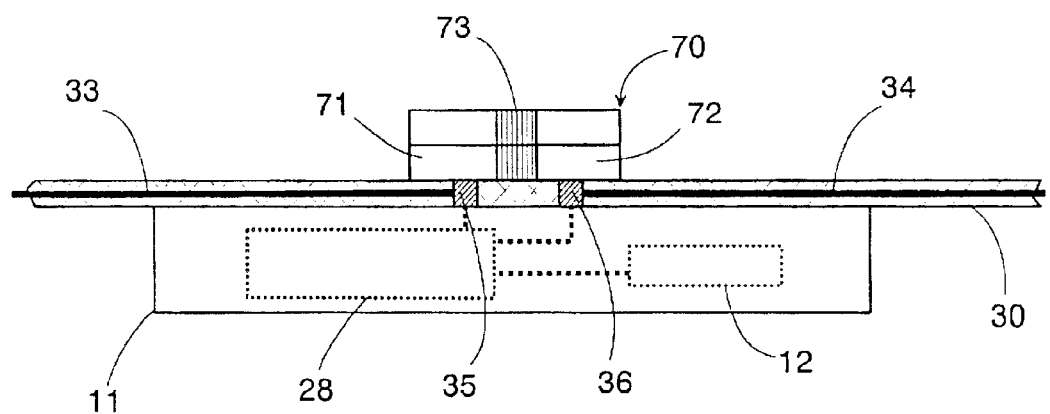
FIG. 9 is a view showing the nameplate as attached to the garment.

As shown in FIG. 7, the case 11 of the transmitter 10 is formed into a nameplate which is made water-tight and accommodates therein the electric circuitry 28 forming the various functional circuits and elements as shown in FIG. 2, and the battery 12 energizing the circuits. The case 11 is provided with a spring-loaded clip 70 so as to be detachable to the garment, for example, at a breast pocket. The clip 70 is pivotally supported at its one end to the case so as to be movable between a pinching position and a release position. The clip 70 includes a pair of conductive terminals 71 and 72 which are connected to the electric circuitry, i.e., across the signal transmitter 16 and which are isolated by a dielectric strip 73. As shown in FIGS. 8 and 9, when the case 11 is attached to the garment, i.e., the breast pocket, the terminals 71 and 72 come into engagement respectively with pads 35 and 36 provided at one ends of respective leads 33 and 34 extending from the individual electrodes 31 and 32. Thus, the electric circuitry of the transmitter is connected to electrodes. In this connection, the leads 33 and 34 are also made of electrically conductive threads, more particularly, strands of the conductive threads sewed on or into the garment 30.

Figure 10:
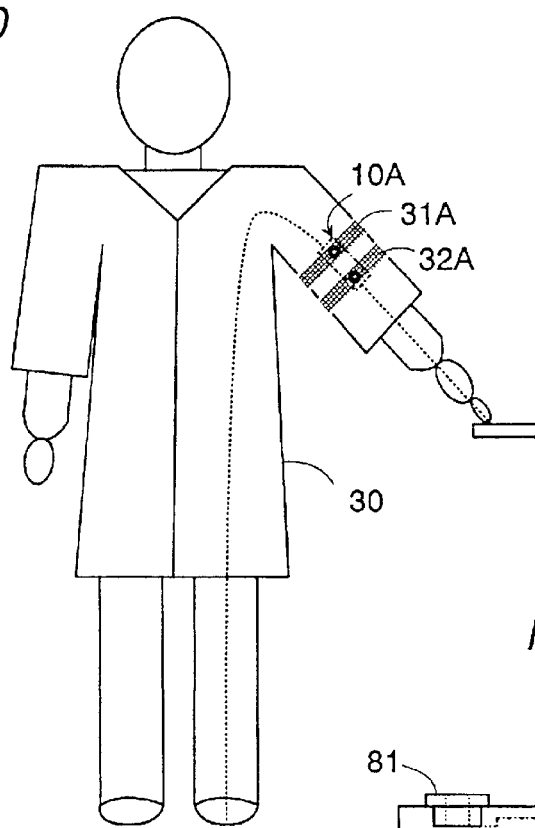
FIG. 10 is schematic view illustrating another embodiment of the system.
Figure 12:
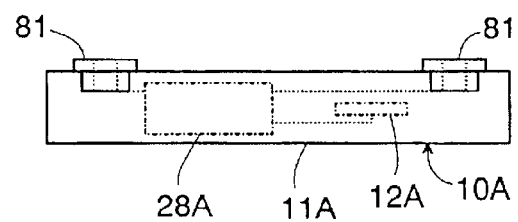
FIG. 12 is a side view of the transmitter case.
Figure 11:
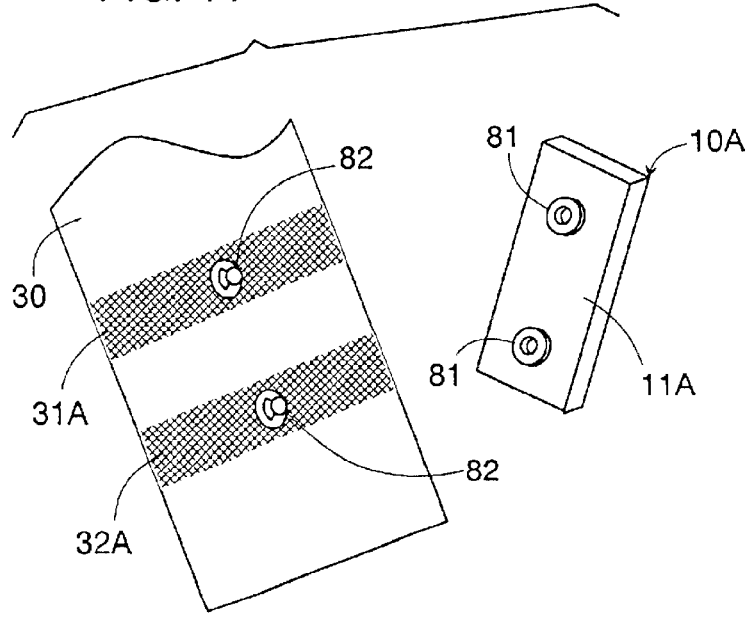
FIG. 11 is an exploded perspective view showing ground and signal electrodes integrated into a sleeve of the garment and a transmitter case detachable thereto.

FIGS. 10 to 12 show another preferred embodiment of the present invention in which a case 11A of the transmitter 10A is detachable to a sleeve of the garment 30 by means of snap buttons which are normally utilized in association with clothing. That is, the snap button is made of conductive material and composed of a socket 81 and a ball 82. In this connection, a ground electrode 31A and a signal electrode 32A are provided at the sleeve of the garment 30 for direct coupling with the electric circuitry of the transmitter 10A. Other structures are identical to the above embodiment and therefore no duplicated explanation is made herein. The case 11A is in the form of a water-tight thin plate accommodating the electric circuitry 28A of the transmitter 10A and the battery 12A. The case 11A is provided with a pair of the sockets 81 which are internally connected to the electrical circuitry of the transmitter 10A, while the electrodes 31A and 32A are provided respectively with the balls 82. As in the previous embodiment, each electrode is made of conductive threads woven and sewed on or into the sleeve to form an annular band surrounding the sleeve in close proximity to the skin of the user wearing the garment for establishing a reliable electrical connection to the human body. In this embodiment, the balls 82 are sewed directly on the electrodes by use of the conductive threads or press-fitted into the electrode, thereby eliminating the leads extending otherwise by a certain distance along the garment from the electrodes. Alternatively, the balls may be provided on the case, or a mixed pair of the ball and socket is provide on the case.

In the illustrated embodiments, the ground and signal electrodes 31 and 32 are explained to be formed by the electrically conductive threads, however, the each electrode may be formed as a metal plating deposited on the surface of the garment or deposited on a fabric which is sewed on the garment. Also, it is noted that the garment into which the electrodes are integrated is not limited to the garment like the white gown and may be any other kinds of the clothing that is constantly worn by the user who is in access to the verified system. Therefore, the clothing may include an armband and wristband integrating the electrodes to which the case of the transmitter can be made electrically and physically detachable by use of the above described snap buttons.

Further, the illustrated embodiments show only one application where both of the electrodes are kept in close facing relation with the skin of the user so that both of the electrodes are in direct electrical connection to the user's body, however, it is equally possible that one of the electrodes is in direct facing relation, i.e., electrical connection to the user's body, while the other of the electrodes is arranged to face away from the user's skin for capacitive connection to the receiver through the air.

Still further, although the illustrated embodiment is arranged to verify the data, i.e., the user's ID at the computer 60, the receiver 40 may be arranged to equip the processor and the data memory so as to have a function of verifying the data from the transmitter, and providing a verified output to an associated device for permitting the access or a required control of the device, for example, permitting an entry of the user into a restricted area.

What is claimed is:

1. A data transmission system using a human body as a signal transmission path, said system comprising a transmitter adapted to be worn on a human body, and a receiver adapted to be connected to an associated device which utilizes data transmitted from the transmitter, said transmitter comprising:

a ground electrode which is placed in close proximity to the human body;

a signal electrode which is placed in close proximity to the human body and in a spatially spaced relation from said ground electrode; and a data memory for storing first data to be transmitted;

a first modulator for converting said first data into a first modulated voltage signal; and a first signal transmitter which applies the first modulated voltage signal across said signal electrode and said ground electrode; and said receiver comprising:

a circuit ground adapted to be connected to the ground;

a touch electrode adapted for direct contact with a portion of the human body carrying said transmitter;

a signal detector connected across said touch electrode and said circuit ground to detect said first modulated voltage signal; and a demodulator for converting said first modulated voltage signal back into said first data, wherein said system includes a garment which is adapted to be worn by a user and integrates said ground and signal electrodes in such a manner that at least one of said ground and signal electrodes is kept in a closely facing relation to the skin of the user, thereby establishing an electrical path extending through a portion of the human body for signal transmission from said transmitter to said receiver, wherein each of said ground and signal electrodes is formed by a plurality of electrically conductive threads and is sewed to be integrated into the garment, and wherein both of said ground and signal electrodes are carried on the garment so as to come into a closely facing relation with the skin of the user, said transmitter including a case which accommodates an electrical circuitry realizing said first modulator and said first signal transmitter and which is formed separately from said ground and signal electrodes, said case being provided with terminals for electrically connecting said electric circuitry with said ground and signal electrodes, and said garment carrying a ground lead and a signal lead which extend respectively from said ground and signal electrodes for connection with said terminals of said case, each said ground and signal leads being formed by a strand of electrically conductive threads and sewed on said garment.

2. The data transmission system as set forth in claim 1, wherein said system includes a coupling means by which said case is detachably connected to said garment and at the same time said electrically circuitry is detachably connected to said ground and signal electrodes, said coupling means comprising a spring-loaded clip which is pivotally supported to said case to be movable between a pinching position and a release position, said clip being provided with said terminals which are electrically isolated from each other for connection respectively with said ground and signal leads at said pinching position.

3. A data transmission system using a human body as a signal transmission path, said system comprising a transmitter adapted to be worn on a human body, and a receiver adapted to be connected to an associated device which utilizes data transmitted from the transmitter, said transmitter comprising:

a ground electrode which is placed in close proximity to the human body;

a signal electrode which is placed in close proximity to the human body and in a spatially spaced relation from said ground electrode; and a data memory for storing first data to be transmitted;

a first modulator for converting said first data into a first modulated voltage signal; and a first signal transmitter which applies the first modulated voltage signal across said signal electrode and said ground electrode; and said receiver comprising:

a circuit ground adapted to be connected to the ground;

a touch electrode adapted for direct contact with a portion of the human body carrying said transmitter;

a signal detector connected across said touch electrode and said circuit ground to detect said first modulated voltage signal; and a demodulator for converting said first modulated voltage signal back into said first data, wherein said system includes a garment which is adapted to be worn by a user and integrates said ground and signal electrodes in such a manner that at least one of said ground and signal electrodes is kept in a closely facing relation to the skin of the user, thereby establishing an electrical path extending through a portion of the human body for signal transmission from said transmitter to said receiver, wherein both of said ground and signal electrodes are carried on the garment so as to come into a closely facing relation with the skin of the user, wherein said transmitter including a case which accommodates an electric circuitry realizing said first modulator and said first signal transmitter and which is formed separately from said ground and signal electrodes, said case being provided with terminals for electrical connecting said electric circuitry respectively with said ground and signal electrodes, and said system including a coupling means by which said case is detachably connected to said garment and at the same time said electrical circuitry is connected to said ground and signal electrodes.

4. The data transmission system as set forth in claim 3, wherein said coupling means comprises a pair of first fasteners each composed of one of a socket and a ball forming a snap button for mounting said case to the garment, a pair of second fasteners each composed of the other of the socket and ball, said first fasteners being fixed on said case and connected across said first signal transmitter, and said second fasteners being fixed on said garment and permanently connected respectively to said ground and signal electrodes.

5. The data transmission system as set forth in claim 4, wherein each of said ground and signal electrodes is formed by a plurality of electrically conductive threads sewed and integrated into the garment, and said second fasteners are held in direct contact with said ground and signal electrodes, respectively.

6. The data transmission system as set forth in claim 5, wherein said ground and signal electrodes are respectively in the form of annular bands provided around a sleeve of the garment in a spaced relation from each other along the length of the sleeve.

7. The data transmission system as set forth in claim 3, wherein said case is made water-tight for sealing said electrical circuitry.

* * * * *